United States Patent [19]

Closse et al.

[11] 4,232,039
[45] Nov. 4, 1980

[54] PHENYL- OR CYCLOALKYL-BENZO-OXACYCLIC COMPOUNDS

[75] Inventors: Annemarie Closse, Binningen; Walter Haefliger, Basel; Daniel Hauser, Binningen, all of Switzerland

[73] Assignee: Sandoz Ltd., Basel, Switzerland

[21] Appl. No.: 896,481

[22] Filed: Apr. 14, 1978

Related U.S. Application Data

[63] Continuation of Ser. No. 795,432, May 10, 1977, abandoned.

[30] Foreign Application Priority Data

May 17, 1976 [CH] Switzerland .......................... 6125/76
Jun. 17, 1976 [CH] Switzerland .......................... 7741/76
Nov. 26, 1976 [CH] Switzerland ........................ 14928/76
Nov. 26, 1976 [CH] Switzerland ........................ 14929/76

[51] Int. Cl.² ................. A61K 31/335; A61K 31/34; C07D 307/79; C07D 313/08
[52] U.S. Cl. .................... 424/278; 424/285; 260/333; 260/346.22
[58] Field of Search .......................... 260/346.22, 333; 424/285, 278

[56] References Cited

U.S. PATENT DOCUMENTS 2,548,704  4/1951  Coleman et al. ................ 260/346.22

FOREIGN PATENT DOCUMENTS 2113489  3/1971  Fed. Rep. of Germany .

OTHER PUBLICATIONS

Weinheimer et al., Tetrahedron Letters, No. 39, pp. 3315–3318 (1969).
Shirasaki et al., Bulletin of Chem. Society of Japan, vol. 46, pp. 2918–2919 (1973).

Primary Examiner—Henry R. Jiles
Assistant Examiner—Bernard Dentz
Attorney, Agent, or Firm—Gerald D. Sharkin; Robert S. Honor; Thomas O. McGovern

[57] ABSTRACT

The invention provides compounds of formula I,

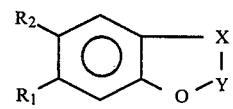

wherein
$R_1$ is branched alkyl, cycloalkyl or phenyl,
$R_2$ is hydrogen, methyl or halogen,
X—Y is —$CHR_3CH_2$—, —$CR_3$=CH— or —$(CH_2)_4$, and
$R_3$ is hydrogen or alkyl, useful, for example, in the treatment of oedemas, inflammation and arthritis.

14 Claims, No Drawings

PHENYL- OR CYCLOALKYL-BENZO-OXACYCLIC COMPOUNDS

This is a continuation of application Ser. No. 795,432, filed May 10, 1977, and now abandoned.

The present invention relates to benzo-furan derivatives.

More particularly, the present invention provides compounds of formula I,

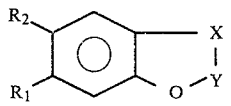

wherein
 $R_1$ is branched alkyl of 3 to 10 carbon atoms, cycloakyl of 3 to 8 carbon atoms or phenyl,
 $R_2$ is hydrogen, methyl, fluorine, chlorine, bromine or iodine,
 X—Y is

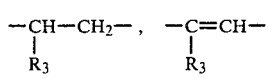

or —(CH$_2$)$_4$—, and
 $R_3$ is hydrogen or alkyl of 1 to 4 carbon atoms,
with the proviso that where $R_2$ is hydrogen and X—Y is —CH=CH—, $R_1$ is other than phenyl and when $R_2$ is hydrogen and X—Y is

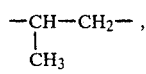

$R_1$ is other than 4-methyl-pentyl.

When $R_1$ is branched alkyl, this preferably contains from 3 to 6 carbon atoms. When $R_1$ is cycloalkyl, this is preferably cyclopentyl or cyclohexyl, especially cyclohexyl.

$R_2$ is preferably halogen or methyl. When $R_2$ is halogen, this is preferably chlorine. In one group of compounds, $R_2$ is hydrogen.

X—Y is preferably

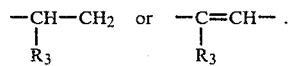

In a second group of compounds, X—Y —(CH$_2$)$_4$—.

When $R_3$ is alkyl, this is preferably methyl. $R_3$ is preferably hydrogen or methyl.

The invention further provides a process for the production of a compound of formula I comprising,
 (a) producing a compound of formula Ia,

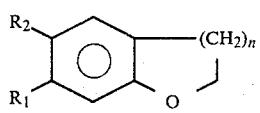

wherein
 n is 1 or 3 and $R_1$ and $R_2$ are as previously defined,
by cyclising a compound of formula II,

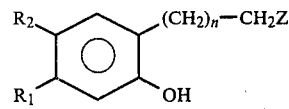

wherein
 Z is a moiety which, with the hydrogen atom of the phenolic hydroxy group, forms an easily removable group HZ, and
 $R_1$, $R_2$ and n are as previously defined,
 (b) producing a compound of formula Ib,

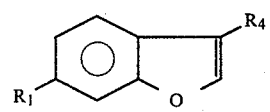

wherein
 $R_4$ is alkyl of 1 to 4 carbon atoms, and
 $R_1$ is as previously defined,
by dehydrating a compound of formula III,

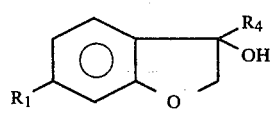

wherein $R_1$ and $R_4$ are as previously defined,
 (c) producing a compound of formula Ic,

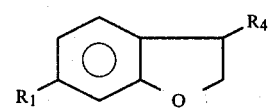

wherein $R_1$ and $R_4$ are as previously defined,
by hydrogenating a compound of formula Ib as previously defined,
 (d) producing a compound of formula Id,

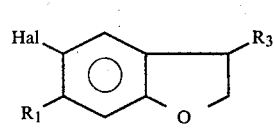

wherein
 Hal is fluorine, chlorine, bromine or iodine, and
 $R_1$ and $R_3$ are as previously defined, by halogenating a compound of formula IV,

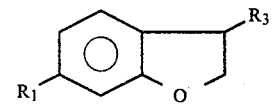

wherein $R_1$ and $R_3$ are as previously defined,
 (e) producing a compound of formula Ie,

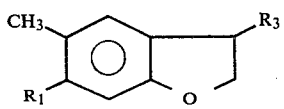

wherein $R_1$ and $R_3$ are as previously defined, by reducing a compound of formula V,

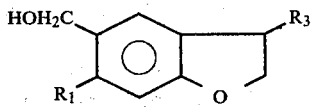

V wherein $R_1$ and $R_3$ are as previously defined, or (f) producing a compound of formula If,

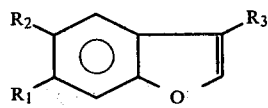

If wherein $R_1$, $R_2$ and $R_3$ are as previously defined, by dehydrogenating a compound of formula VI,

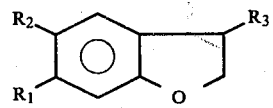

VI wherein $R_1$, $R_2$ and $R_3$ are as previously defined.

In process variant (a), the cyclisation is effected in the presence of a base, preferably a base containing a tertiary nitrogen atom or in sodium acetate. Suitable tertiary nitrogen atom bases include, for example, pyridine, triethylamine and especially 1,5-diazabicyclo[5,4,-0]undec-5-ene. The reaction may advantageously be effected in an inert organic solvent or, if desired, in an excess of the tertiary organic base. The reaction may suitably be effected at a temperature of from 20° to 100° C. The preferred solvent is methylene chloride; in the case of sodium acetate, the preferred solvent is ethanol.

Z can, for example, be chlorine, bromine or iodine, especially bromine.

The compounds of formula II may be obtained by reducing compounds of formula VII,

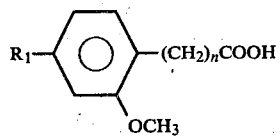

VIII optionally after previous esterification and halogenation or methylation [for example, as in process variant (d) or (e)], in known manner (for example, with LiAlH$_4$ or diborane) to produce compounds of formula VIII,

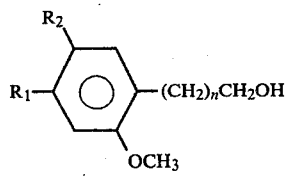

VIII followed by introduction of the group Z (e.g. with BBr$_3$) with a simultaneous substitution of the methoxy group with a hydroxy group.

The compounds of formula VII, wherein $n=3$, can be prepared by reacting a compound of formula IX,

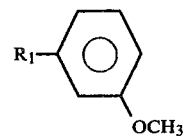

IX with succinic acid to produce a compound of formula X,

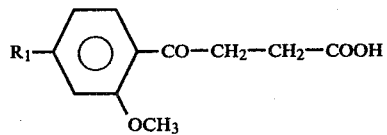

X followed by reduction of the keto group to a hydroxy group according to known methods (e.g. with NaBH$_4$) and finally, hydrogenating the resulting compounds in known manner, to produce the compound of formula VII wherein $n=3$.

The dehydration according to process variant (b) can be effected by known methods, in part by simple acidification of the hydroxy compound, or, for example, in the presence of a catalytic amount of a strong acid such as p-toluenesulphonic acid. The reaction is effected in the presence of an inert organic solvent such as benzene or toluene. For complete elimination of water, the reaction mixture should be heated to boiling.

The compounds of formula III can, for example, be prepared by (a) effecting a Friedel-Crafts reaction between a compound of formula IX, previously referred to, and chloroacetyl chloride to produce a compound of formula XI,

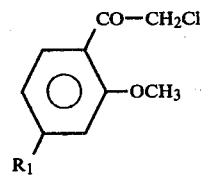

XI (b) splitting off the methyl group from the compound of formula XI with the aid of BBr$_3$ and finally cyclising the resulting compound in the presence of sodium acetate at an elevated temperature to yield a compound of formula XII,

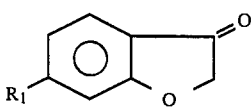

(c) thecompound of formula XII is converted, according to known methods, to a compound of formula XIII with a Griguard reagent $R_4MgHal$,

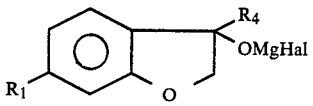

(d) the compound of formula XIII can be hydrolysed according to known methods, e.g. by pouring the ethereal solution into ice/water. Not only compounds of formula III can be produced by the hydrolysis, but also compounds of formula Ib, especially if the conditions are acidic.

The hydrogenation according to process variant (c) can be effected by known methods for the obtention of 2,3-dihydrobenzofurans from benzofurans. Preferably, the hydrogenation is carried out in the presence of a rare metal catalyst. A preferred catalyst is palladium on charcoal. The reaction is preferably effected in an inert solvent such as ethyl acetate or a lower alcohol, suitably at a temperature between room temperature and the boiling temperature of the reaction mixture and either at standard pressure or under a slight excess pressure.

The halogenation according to process variant (d) can be effected by known methods. For example, the compound of formula IV can be chlorinated or brominated with sulphuryl chloride or bromide, preferably in the presence of Kieselgel, or with chlorine or bromine gas in the presence of a Friedel-Crafts catalyst. The reaction is preferably effected in an inert organic solvent, for example, methylene chloride, at a temperature of from 0° C. to the boiling temperature of the reaction mixture.

Iodination can be effected with ICl in the presence of an acid, e.g. $CH_3COOH$.

Fluorination of the compounds of formula IV may suitably be effected by nitrating these compounds, e.g. with $HNO_3$ in $CH_2Cl_2$ at a temperature of from $-20°$ to $+50°$ C., and reducing the resulting 5-nitro compounds to the corresponding 5-amino compounds, for example, by catalytic hydrogenation in the presence of palladium. The amino compounds are then converted to the fluorides according to the Schieman reaction, whereby a diazotisation in the presence of a fluoroborate is effected and the resulting diazonium fluoroborates decomposed by heating to yield the fluoride compounds.

The hydrogenation according to process variant e) is effected in the presence of a rare earth catalyst, preferably palladium on charcoal, according to known methods. The hydrogenation takes place in an inert solvent such as a lower alcohol or ethyl acetate. A slight excess pressure (ca. 3 atm) of hydrogen is preferably employed.

The compounds of formula V can be prepared by formylating a compound of formula IV, e.g. with dichloromethyl methyl ether to yield compounds of formula XIV,

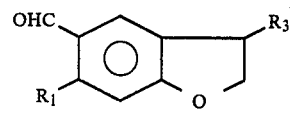

and reducing these compounds, e.g. with $NaBH_4$, to provide the compounds of formula V.

The dehydrogenation according to process (f) is effected in the presence of a dehydrogenating agent according to known methods. Examples of suitable dehydrogenating agents are palladium on charcoal, 2,3-dichloro-5,6-dicyanol-1,4-benzoquinone or chloranil. The reaction may advantageously be effected in an inert solvent such as dioxane, acetic acid, toluene or p-cymol at the boiling point of the reaction mixture.

Insofar as the production of the starting materials is not described, these are either known or may be produced in accordance with known processes, or in manner analogous to the processes described herein, or to known processes.

In the following non-limitative Examples, all temperatures are indicated in degrees Celsius.

EXAMPLE 1

5-Chloro-6-cyclohexyl-2,3-dihydro-benzofuran

[Process variant a)]

1.84 ml of 1,5-diazabicyclo[5,4,0] undec-5-en are added at 0° to 4.4 g of 1-bromo-2-(5-chloro-4-cyclohexyl-2-hydroxyphenyl)-ethane in 100 ml of methylene chloride. After stirring for 2 hours at 22°, there is substantial evaporation and the residue is chromatographed on 60 g of silica gel. The product, which is eluted with methylene chloride, is distilled in a bulb tube. Pure 5-chloro-6-cyclohexyl-2,3-dihydro-benzofuran comes over at 140°/0.1 mm. M.p. 84°-85°.

NMR Spectrum ($CDCl_3$): 1.1–1.9 (10H), 2.94 b (1H), 3.11 t (2H), 4.51 t (2H), 6.7 s (1H), 7.1 s (1H).

The 1-bromo-2-(5-chloro-4-cyclohexyl-2- hydroxyphenyl)-ethane used as the starting material is produced as follows:

(a) (4-Cyclohexyl-2-methoxyphenyl)-acetic acid methylester

A solution of 20 g of (4-cyclohexyl-2-methoxyphenyl)-acetic acid in 200 ml of dry methanol is saturated with HCl gas at 0°. After standing at 22° for 18 hours, it is evaporated to dryness.

The residue is chromatographed on 500 g of silica gel. A homogeneous product is extracted with methylene chloride.

(b) (5-Chloro-4-cyclohexyl-2-methoxyphenyl)-acetic acid methylester

The (4-cyclohexyl-2-methyoxyphenyl)-acetic acid methylester obtained as above is dissolved in 500 ml of methylene chloride, and 5.5 ml of sulphuryl chloride and 200 mg of silica gel are added. After stirring at 22° for 60 hours, there is substantial evaporation, and the residue is chromatographed on 300 g of silica gel. A homogeneous product is extracted with methylene chloride.

(c)
2-(5-Chloro-4-cyclohexyl-2-methoxyphenyl)-ethanol 7 g of LiAlH$_4$ are added in portions at 0° under an inert gas atmosphere to 16 g of (5-chloro-4- cyclohexyl-2-methoxyphenyl)-acetic acid methyl ester in 350 ml of dry tetrahydrofuran. Stirring is then effected for 18 hours at 22°. 20 ml of ethyl acetate are carefully added in drops so as to destroy the excess LiAlH$_4$. The mixture is then poured onto a solution of NH$_4$Cl in ice water, acidified with 2N H$_2$SO$_4$ and extracted three times with acetic ester. The organic phases are washed with water, dried over Na$_2$SO$_4$ and concentrated. The residue is chromatographed on 250 g of silica gel. The product, which is extracted with methylene chloride, is distilled in a bulb tube. M.p. 78°–79°.

(d)
1-Bromo-2-(5-chloro-4-cyclohexyl-2-hydroxyphenyl)-ethane 20 ml of boron tribromide are added slowly at 0° with stirring to 11 g of 2-(5-chloro-4-cyclohexyl-2- methoxyphenyl)-ethanol in 300 ml of dry methylene chloride. The mixture is then stirred for 5 hours at 22°.

The reaction mixture is poured onto ice/water and extracted three times with methylene chloride. The organic phases are washed with water, dried over Na$_2$SO$_4$ and concentrated. The residue is chromatographed on 200 g of silica gel. 1-Bromo-2-(5-chloro-4-cyclohexyl- 2-hydroxyphenyl)-ethane is extracted with methylene chloride M.p. 7°–78°.

Starting with the corresponding compounds of formula II, the following compounds may be obtained in a similar manner by cyclisation:

EXAMPLE 2

6-Cyclohexyl-2,3-dihydro-benzofuran

NMR Spectrum (CDCl$_3$): 1.1–2.1 (10H), 2.45 b (1H), 3.16 t (J=9Hz, 2H), 4.55 t (J=9Hz, 2H), 6.6–7.2 (3H).

The 1-bromo-2-(4-cyclohexyl-2-hydroxyphenyl)-ethane used as the starting material is produced by the reduction of (4-cyclohexyl-2-methoxyphenyl)-acetic acid with diborane, and subsequent reaction with BBr$_3$.

EXAMPLE 3

6-Cyclohexyl-2,3-dihydro-5-methyl-benzofuran

NMR Spectrum (CDCl$_3$): 1.2–1.9 (10H), 2.23 s (3H), 2.64 b (1H), 3.11 t (2H), 4.49 t (2H), 6.66 s (1H), 6.93 s (1H).

The 1-bromo-2-(4-cyclohexyl-2-hydroxy-5-methylphenyl)-ethane used as the starting material is produced as follows:

(4-cyclohexyl-2-methoxyphenyl)-acetic acid is reacted with 1,1-dichlormethyl-methylester, the resulant 5-formyl compound is reduced with NaBH$_4$ to form the corresponding 5-hydroxymethyl derivatives, then hydrogenated to form the 5-methyl compound and subsequently treated as in the previous Example with diborane and then with BBr$_3$.

EXAMPLE 4

5-Chloro-2,3-dihydro-6-phenyl-benzofuran

NMR Spectrum (CDCl$_3$): 3.17 t (2H), 4.54 t (2H), 6.69 s (1H), 7.19 s 7.33 (5H).

The starting material is produced in manner analogous to those described in the previous Examples.

EXAMPLE 5

2,3-Dihydro-5-methyl-6-phenyl-benzofuran

NMR Spectrum (CDCl$_3$): 2.15 s (3H), 3.19 t (2 H), 4.54 t (2H), 6.65 s (1H), 7.05 s (1H), 7.3 (5H).

The starting material is produced in manner analogous to those described in the previous Examples.

EXAMPLE 6

7-Chloro-8-cyclohexyl-2,3,4,5-tetrahydro-1-benzoxepin

NMR Spectrum (CDCl$_3$): 1.2–2.0 (14H), 2.65–3.1 m (3H), 3.96 (2H), 6.86 s (1H), 7.06 s (1H).

The 1-bromo-4-(5-chloro-4-cyclohexyl-2-hydroxyphenyl)-butane used as the starting material is produced as follows:

(a) 4-Oxo-4-(4-cyclohexyl-2-methoxyphenyl)-butyric acid 70 g of AlCl$_3$ are added with stirring at −5° to 47.5 g of m-cyclohexylanisole, 26.5 g of succinic acid anhydride, 250 ml of tetrachloroethane and 62.5 ml of nitrobenzene, at such a rate that the temperature does not exceed −5°. The mixture is then stirred for 72 hours at 22°. 2N hydrochloric acid is then slowly added in the cold to the reaction solution until there is no further reaction, and the solution is then extracted twice with methylene chloride. The organic phases are extracted with 2N NaOH. The alkaline extract is acidified and extracted there times with ethyl acetate. The ethyl acetate phases are washed three times with water, dried over Na$_2$SO$_4$ and evaporated. The residue is crystallised twice from methylene chloridehexane. M.p. 130°–131°.

NMR Spectrum (CDCl$_3$): 1.1–2.0 b (10H), 2.50 b (1H), 2.69 t (J=7Hz, 2H), 3.27 t (J=7Hz), 3.9 s (3H), 6.75 s (1H), 6.8 d (J=8Hz, 1H), 7.7 d (J=8Hz, 1H).

(b)
4-Hydroxy-4-(4-cyclohexyl-2-methoxyphenyl)-butyric acid 1.06 g of NaBH$_4$ in 90 ml of dioxane-water (1:1) are added dropwise with stirring at room temperature to 1.16 g of 4-oxo-4-(4-cyclohexyl-2-methoxyphenyl)-butyric acid in 200 ml of dioxane-water (1:1). This is left to stand for 5 hours at 22° and then acidified with 2N H$_2$SO$_4$ to pH=2. Most of the dioxane is removed on rotary vapouriser and the aqueous solution is extracted three times with ethyl acetate. The organic phases are washed once with water, dried over Na$_2$SO$_4$ and concentrated. The residue is recrystallised twice from ether-petroleum-ether. M.p. 105°–106°.

NMR Spectrum (CDCl$_3$): 1.2–2.6 b (15H), 3.83 s(3H), 4.89 t (J=6Hz, 1H), 6.71 s (1H), 6.78 d (J=8Hz, 1H), 7.18 d (J=8Hz, 1H).

(c) 4-(4-Cyclohexyl-2-methoxyphenyl)-butyric acid 1 g of 4-hydroxy-4-(4-cyclohexyl-2-methoxyphenyl)-butyric acid is dissolved in 20 ml of ethyl acetate and hydrogenated in the presence of 100 mg of Pd on carbon (10%). When the hydrogen has been completely absorbed, filtration takes place. The filtrate is evaporated and the residue is recrystallised from CH$_2$Cl$_2$-pentane. M.p. 104°–105°.

NMR Spectrum (CDCl$_3$): 1.1–2.8 b (17H), 3.80 s (3H), 6.60–7.10 (3H).

(d)
4-(5-Chloro-4-cyclohexyl-2-methoxyphenyl)-butyric acid methylester 7.8 g of 4-(4-cyclohexyl-2-methoxyphenyl)-butyric acid are dissolved in 700 ml of anhydrous methanol and saturated whilst cooling with HCl gas. After 48 hours and with the exclusion of moisture, the mixture is evaporated under vacuum and the residue dissolved in 400 ml of methylene chloride. 2.4 ml of sulphuryl chloride and 500 ml of silica gel are added whilst cooling and stirring. After stirring for 18 hours at 20°, the mixture is filtered and the residue is concentrated until dry.

(e)
4-(5-Chloro-4-cyclohexyl-2-methoxyphenyl)-butan-1-ol 4 g of LiAlH$_4$ are added in portions at 0° with stirring, and in an inert gas atmosphere, to 8.6 g of 4-(5-chloro-4-cyclohexyl-2-methoxyphenyl)-butyric acid methylester in 300 ml of anhydrous tetrahydrofuran. After 24 hours at 20°, the mixture is poured onto icecold NH$_4$CL solution. The mixture is then acidified to pH=3 and extracted three times with ethyl acetate. The organic phases are washed once with water, dried over Na$_2$SO$_4$ and concentrated. The residue is distilled at 170°/0.5 mm.

(f)
1-Bromo-4-(5-chloro-4-cyclohexyl-2-hydroxyphenyl)-butane 1.7 ml of bromine are added dropwise at 0° to 10.23 g of triphenyl phosphite in anhydrous ether. After 10 minutes, the residue is filtered, washed with ether, dried, dissolved in methylene chloride and then, at 0°, a solution of 4.5 g of 4-(5-chloro-4-cyclohexyl-2-methoxyphenyl)-butan-1-ol and 2.64 g of pyridine in methylene chloride is added dropwise. After stirring for 18 hours at 20°, the mixture is evaporated and the residue chromatographed on 150 g of silica gel. The product, which is extracted with toluene, is dissolved in 150 ml of methylene chloride and then, at 0°, 10 ml of BBr$_3$ are slowly added with stirring. After stirring for 2 hours at 20°, the mixture is poured onto ice/water and extracted three times with methylene chloride. The organic phases are washed once with water, dried over Na$_2$SO$_4$ and concentrated, whereby the title compound is obtained.

EXAMPLE 7

7-Chloro-2,3,4,5-tetrahydro-8-phenyl-1-benzoxepin

NMR Spectrum (CDCl$_3$): 1.5–2.1 (4H), 2.80 (2H), 4.01 (2H), 6.98 s (1H), 7.21 s (1H), 7.39 (5H). M.p. 69°–70°.

The 1-bromo-4-(5-chloro-2-hydroxy-4-biphenyl)-butane used as the starting material is produced in manner analogous to that employed for 1-bromo-4-(5-chloro-4-cyclohexyl-2-hydroxy-phenyl)-butane from 3-methoxy-biphenyl.

EXAMPLE 8

6-Cyclohexyl-3-methyl-benzofuran

[Process variant b)]

14.4 g of magnesium filings are suspended in 500 ml of ether (absolute), then 20 mg of iodine are added, and the Grignard reagent is produced by slowly adding dropwise 36.6 ml of methyl iodide. After 60 minutes, an ethereal solution of 40 g of 6-cyclohexyl-2,3-dihydrobenzofuran-3-one is added dropwise and stirred for 48 hours at 22°. The mixture is then refluxed for 2 hours, the reaction mixture poured onto ice/water, slightly acidified with acetic acid and then extracted three times with ethyl acetate. The organic phases are washed with water, dried over Na$_2$SO$_4$ and evaporated. The residue is chromatographed on 1 kg of silica gel. The product, which is extracted with toluene, is distilled in a bulb tube at 130°/0.1 mm.

NMR Spectrum (CDCl$_3$): 1.1–2.1 (10H), 2.20 s (3H), ca. 2.6 (1H), 7.05–7.43 (4H).

The 6-cyclohexyl-2,3-dihydro-benzofuran-3-one employed as starting material can be produced as follows:

50 g of 3-cyclohexylanisole are dissolved in 500 ml of absolute methylene chloride, cooled at 0° and 42.5 g of aluminium trichloride are added. 41.8 ml of chloracetyl chloride are added under vigorous stirring and, after five hours, a further 42.5 g of aluminium trichloride are added. The reaction mixture is left to warm to a temperature of 20° and stirred for 25 hours. The mixture is poured onto ice and extracted three times with methylene chloride. The organic phases are washed with water, dried over Na$_2$SO$_4$ and reduced in volume. The oily residue is dissolved in 500 ml of absolute methylene chloride cooled to −50° and 30 ml of boron tribromide are added. The mixture is further stirred for 3 hours at 22°. The reaction mixture is poured onto ice-water and extracted three times with methylene chloride. The organic phases are washed with water, dried over Na$_2$SO$_4$ and reduced in volume. The oily residue together with 50.0 g of sodium acetate in 600 ml of ethanol are refluxed with stirring for 25 hours. After cooling, the solvent is removed, and the product partitioned between water and ethyl acetate and then leached three times with water. The aqueous phases are again extracted with ethyl acetate, the organic phases combined, dried over Na$_2$SO$_4$ and reduced in volume. The residue is chromatographed on 1.5 kg of Kieselgel and 6-cyclohexyl-2,3-dihydrobenzofuran-3-one eluted with toluene. After crystallizing out from a small amount of hexane, the product melts at 47°–50°.

EXAMPLE 9

6-Cyclohexyl-2,3-dihydro-3-methyl-benzofuran

[Process variant c)]

9.2 g of 6-cyclohexyl-3-methyl-benzofuran are dissolved in 140 ml of ethyl acetate and hydrogenated in the presence of palladium (10% on active charcoal). After 5 hours, the mixture is filtered and reduced in volume. 6-Cyclohexyl-2,3-dihydro-3-methyl-benzofuran is obtained as an oily product by distillation in a bulb tube at 120°/0.1 mm.

NMR Spectrum (CDCl$_3$): 1.0–2.0 (13H), ca. 2.43 (1H), 3.48 (1H), 4.03 t (1H), 4.64 t (1H), 6.64–7.20 (3H).

EXAMPLE 10

5-Chloro-6-cyclohexyl-2,3-dihydro-3-methyl-benzofuran

[Process variant d)]

6.2 g of 6-Cyclohexyl-2,3-dihydro-3-methyl-benzofuran are dissolved in 350 ml of a methylenechloride and 200 mg of Kieselgel and 2.32 g of sulphuryl chloride are added. After stirring for 25 hours at 22°, the mixture is filtered and the filtrate reduced in volume. The residue is distilled in a bulb tube at 140°/0.1 mm.

EXAMPLE 11

6-Cyclohexyl-2,3-dihydro-5-methyl-benzofuran

[Process variant e)]

2 g of Cyclohexyl-2,3-dihydro-5-hydroxymethyl-benzofuran are dissolved in 100 ml of ethanol and hydrogenated for 18 hours in the presence of 0.5 g of palladium on charcoal (10%) under a pressure of 3 atm. The reaction solution is filtered and reduced in volume and the residue chromatographed on Kieselgel. The pure title compound is eluted with methylene chloride.

NMR Spectrum: see Example 3.

The 6-cyclohexyl-2,3-dihydro-5-hydroxymethyl-benzofuran may be prepared as follows:

5 g of 6-Cyclohexyl-2,3-dihydro-benzofuran are dissolved in methylene chloride. 9.5 ml of $TiCl_4$ are slowly added dropwise whilst cooling and stirring, followed by 2.9 g of dichloromethylmethylether in 10 ml of $Ch_2Cl_2$. The mixture is stirred for 5 hours at 22°, poured onto ice-water and extracted with ethyl acetate. The organic phase is washed with water, dried over $Na_2SO_4$ and reduced in volume. The residue is dissolved in tetrahydrofuran without further purification. An excess of $NaBH_4$ is added and the mixture refluxed for 3 hours. Natural working of the mixture yields 6-cyclohexyl-2,3-dihydro-5-hydroxymethyl-benzofuran.

EXAMPLE 12

5-Chloro-6-cyclohexyl-3-methyl-benzofuran

[Process variant f)]

5.2 g of 5-Chloro-6-cyclohexyl-2,3-dihydro-3-methyl-benzofuran are dissolved in 400 ml of dioxane and 4.7 g of 2,3-dichloro-5,6-dicyano-1,4-benzoquinone added. The mixture is refluxed for 18 hours, left to cool and filtered. The filtrate is evaporated and the residue chromatographed. 5-Chloro-6-cyclohexyl-3-methyl-benzofuran is eluted with toluene and distilled in a bulb tube at 130°/0.1 mm.

NMR Spectrum ($CDCl_3$): 1.1–2.1 (10H), 2.16 s (3H), ca. 3.1 (lH), 7.30–7.44 (3H).

EXAMPLE 13

5-Chloro-6-cyclohexyl-benzofuran

The title compound is obtained from 5-chloro-6-cyclohexyl-2,3-dihydro-benzofuran in manner analogous to that described in Example 12. M.p. 28°–30°.

NMR Spectrum ($CDCl_3$): 1.0–2.1 (10H), 3.1 b (1H), 6.65 (1H), 7.39 (1H), 7.55 (2H).

EXAMPLE 14

5-Methyl-6-phenyl-benzofuran 830 mg of 2,3-Dihydro-5-methyl-6-phenyl-benzofuran and 100 mg of palladium on charcoal are refluxed for 48 hours in 10 ml of freshly distilled p-cymol. After cooling, the mixture is filtered through talc and the filtrate evaporated. The residue is chromatographed on 15 g of Kieselgel. 5-Methyl-6-phenyl-benzofuran is eluted with toluene as a uniformly oily liquid.

NMR Spectrum ($CDCl_3$): 2.30 (3H), 6.71 (1H), 7.1–7.6 (8H).

The following compounds may be obtained by dehydrogenating the appropriate compound of formula VI in manner analogous to that described above.

EXAMPLE 15

6-Cyclohexyl-5-methyl-benzofuran

NMR Spectrum ($CDCl_3$): 1.2–2.1 (10H), 2.38 s (3H), 2.75 b (1H), 6.62 (1H), 7.2–7.5 (3H).

EXAMPLE 16

5-Chloro-6-phenyl-benzofuran

NMR Spectrum ($CDCl_3$): 6.78 (1H), 7.2–7.7 (8H).

EXAMPLE 17

2,3-Dihydro-6-isobutyl-benzofuran

[Process variant a)]

The title compound may be obtained by cyclising the appropriate compound of formula II in manner analogous to that described in Example 1.

NMR Spectrum ($CDCl_3$): 0.88 d (6H), 1.83 m (1H), 2.41 d (2H), 3.14 t (2H), 4.52 t (2H), 6.5–7.1 (3H).

EXAMPLE 18

5-Chloro-2,3-dihydro-6-isopropyl-benzofuran

[Process variant a)]

The title compound may be obtained by cyclising the appropriate compound of formula II in manner analogous to Example 1.

NMR Spectrum ($CDCl_3$): 1.20 d (6H), 3.0–3.6 m (3H), 4.58 t (2H), 6.75 (1H), 7.17 (1H).

The compounds of formula I are useful because they possess pharmaceutical activity in animals. In particular, they exhibit oedema and inflammation inhibitory, as well as anti-arthritic, activity as indicated in standard tests, e.g. the carrageen paw oedema test, the adjuvans arthritis test, the sub-chronic granuloma cyst test in the rat and in the U.V. erythema test in the guinea pig. Satisfactory results are obtained in these tests on administration p.o. of from about 0.5 to about 100 mg/kg, suitably from about 0.5 to about 30 mg, and preferably from about 0.5 to about 10 mg/kg animal body weight of the compounds. The compounds exhibit an activity spectrum similar to known non-steroidal antiphlogistic agents, such as Indomethazin and Phenylbutazone. The compounds also similarly exhibit an anti-pyretic effect, e.g. in the yeast fever rat test, and an anti-analgesic effect. The compounds similarly inhibit in vitro P.G. synthetase and Collagen induced blood platelet aggregation.

The compounds are therefore useful as anti-phlogistics as well as anti-arthritics, analgesics, anti-pyretics and blood platelet aggregation inhibitors.

For the above mentioned uses, the dosage will, of course, vary depending on the compound employed, mode of administration and therapy desired. However, in general, satisfactory results are obtained when administered at a daily dosage of from about 0.5 to about 100 mg/kg, suitably from about 0.5 to about 30 mg/kg, and preferably from about 0.5 to about 10 mg/kg animal body weight, conveniently given in divided doses 2 to 4 times a day or in sustained release form. For the larger mammal, the total daily dosage is in the range from about 20 to about 3000 mg, suitably from about 20 to about 1000 mg, preferably from about 20 to about 300 mg, and dosage forms suitable for oral administration comprise from about 5 to about 150 mg of the compounds admixed with a solid or liquid pharmaceutical carrier or diluent.

The compound of Example 13 is particularly interesting.

The present invention also provides a pharmaceutical composition comprising a compound of formula I, in association with a pharmaceutically acceptable diluent or carrier. Such compositions may be in the form of, for example, a solution or a capsule.

In one group of compounds, X—Y is—$(CH_2)_n$—, wherein n is 1 or 3 and $R_1$ and $R_2$ are as previously defined.

In a second group of compounds, X—Y is—CH=CH— and $R_1$ and $R_2$ are as previously defined.

In a third group of compounds, X—Y is —CH$R_3$—CH$_2$—, wherein $R_1$ is as previously defined, $R_2$ is chlorine or bromine and $R_3$ is methyl of 1 to 4 carbon atoms.

When $R_1$ is branched alkyl, this may be alkyl of 3 to 5 carbon atoms. In a further group of compounds, $R_1$ may be branched alkyl of 3 or 4 carbon atoms.

When X—Y is —C$R_3$=CH—, $R_3$ may be alkyl of 1 to 4 carbon atoms.

What is claimed is:

1. A compound of formula I

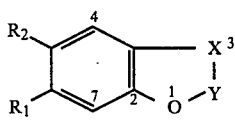

where
$R_1$ is cycloalkyl of 3 to 8 carbon atoms or phenyl,
$R_2$ is methyl or chloro,
X—Y is

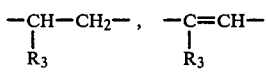

or—$(CH_2)_4$—, and
$R_3$ is hydrogen or alkyl of 1 to 4 carbon atoms, with the proviso that when X—Y is

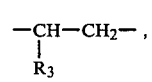

$R_2$ is chloro when $R_3$ is hydrogen.

2. 5-Chloro-6-cyclohexyl-benzofuran.
3. A compound of claim 1 which is 5-chloro-6-cyclohexyl-2,3-dihydro-benzofuran.
4. A compound of claim 1 which is 5-chloro-2,3-dihydro-6-phenyl-benzofuran.
5. A compound of claim 1 which is 7-chloro-8-cyclohexyl-2,3,4,5-tetrahydro-1-benzoxepin.
6. A compound of claim 1 which is 7-chloro-2,3,4,5-tetrahydro-8-phenyl-1-benzoxepin.
7. A compound of claim 1 which is 5-chloro-6-cyclohexyl-2,3-dihydro-3-methyl-benzofuran.
8. A compound of claim 1 which is 5-chloro-6-cyclohexyl-3-methyl-benzofuran.
9. A compound of claim 1 which is 5-methyl-6-phenyl-benzofuran.
10. A compound of claim 1 which is 6-cyclohexyl-5-methyl-benzofuran.
11. A compound of claim 1 which is 5-chloro-6-phenyl-benzofuran.
12. A compound of claim 1 which is 6-cyclohexyl-2,3-dihydro-5-methyl-benzofuran.
13. A pharmaceutical composition comprising an anti-oedemic, anti-inflammatory or anti-arthritic amount of a compound of claim 1, in association with a pharmaceutically acceptable diluent or carrier.
14. A method of treating oedemas, inflammation and arthritis in animals in need of said treatment which comprises administering an anti-oedemas, anti-inflammatory or anti-arthritic effective amount of a compound of formula I

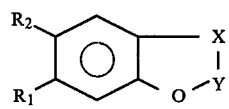

wherein
$R_1$ is branched alkyl of 3 to 10 carbon atoms, cycloalkyl of 3 to 8 carbon atoms or phenyl,
$R_2$ is hydrogen, methyl, fluorine, chlorine, bromine or iodine,
X—Y is

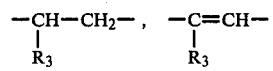

or—$(CH_2)_4$—, and
$R_3$ is hydrogen or alkyl of 1 to 4 carbon atoms, with the proviso that where $R_2$ is hydrogen and X—Y is—CH=CH—, $R_1$ is other than phenyl and when $R_2$ is hydrogen and X—Y is

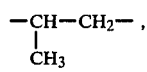

$R_1$ is other than 4-methyl-pentyl.

* * * * *